(12) United States Patent
Tian

(10) Patent No.: US 9,862,991 B2
(45) Date of Patent: *Jan. 9, 2018

(54) GENE SYNTHESIS PROCESS, GENE CHIP AND KIT

(75) Inventor: Jingdong Tian, Beijing (CN)

(73) Assignee: Jingdong Tian, Beijing (CN)

( * ) Notice: Subject to any disclaimer, the term of this patent is extended or adjusted under 35 U.S.C. 154(b) by 419 days.

This patent is subject to a terminal disclaimer.

(21) Appl. No.: 14/384,960

(22) PCT Filed: Apr. 17, 2012

(86) PCT No.: PCT/CN2012/074181
§ 371 (c)(1),
(2), (4) Date: Sep. 12, 2014

(87) PCT Pub. No.: WO2013/134984
PCT Pub. Date: Sep. 19, 2013

(65) Prior Publication Data
US 2015/0031088 A1    Jan. 29, 2015

(30) Foreign Application Priority Data
Mar. 15, 2012  (CN) .......................... 2012 1 0068841

(51) Int. Cl.
C12Q 1/68 (2006.01)
C12N 15/10 (2006.01)
C12P 19/34 (2006.01)
C12N 15/66 (2006.01)

(52) U.S. Cl.
CPC ........... *C12Q 1/6837* (2013.01); *C12N 15/10* (2013.01); *C12N 15/66* (2013.01); *C12P 19/34* (2013.01)

(58) Field of Classification Search
None
See application file for complete search history.

(56) References Cited

U.S. PATENT DOCUMENTS

2005/0089900 A1    4/2005 Fujisaki et al.

FOREIGN PATENT DOCUMENTS

| CN | 1257918 A   | 6/2000 |
|----|-------------|--------|
| WO | 02/36823 A1 | 5/2002 |

OTHER PUBLICATIONS

Saeem, Ishtiaq. Enabling Technologies for Synthetic Biology: Gene Synthesis and Error-Correction from a Microarray-Microfluidic Integrated Device. 2011. Dissertation submitted in the Department of Biomedical Engineering, Duke University.*
Hu, Na et al. "Application of Gene Chips in Analysis of Differential Expressions of Genes Involving in Aflatoxin Biosynthesis" In: China Academic Journal Electronic Publishing House 2009, vol. 30, No. 17 pp. 208-211.
Richmond, Kathryn et al. "Amplification and assembly of chip-eluted DNA (AACED): a method for high-throughput gene synthesis" In Nucleic Acids Research Sep. 24, 2004, vol. 32, No. 17 pp. 5011-5018.
Tian, Jing-Dong "Gene synthesis technology and synthetic biology" In: Chinese Bulletin of Life Science Sep. 2011, vol. 23. No. 9, pp. 931-934.
Zhou, Xiaochuan et al. "Microfluidic PicoArray synthesis of oligodeoxynucleotides and simultaneous assembling of multiple DNA sequences" In Nucleic Acids Research , Oct. 11, 2004, vol. 32, No. 18 pp. 5409-5417.
Quan, Jiayuan et al. "Parallel on-chip gene synthesis and application to optimization of protein expression" In: Nature Biotechnology May 2011, vol. 29. No. 5, pp. 449-453.
International Search Report for PCT/CN2012/074181 dated Dec. 20, 2012.
European Search Report for EP 12871271 dated Sep. 28, 2015.
Saaem, Ishtiaq et al.: "Error correction of microchip synthesized genes using Surveyor nuclease" In: Nucleic Acids Research, Nov. 29, 2011, vol. 40, No. 3. pp. 1-8.
Ma, Siying et al.: "Error correction in gene synthesis technology" In: Trends in Biotechnology, Mar. 2012, vol. 30, No. 3, pp. 147-154.

* cited by examiner

*Primary Examiner* — Angela M Bertagna
(74) *Attorney, Agent, or Firm* — Pearne & Gordon LLP

(57) ABSTRACT

Provided is a chip process of gene synthesis, and the process comprises incorporating the whole procedure, which comprises amplifying oligonucleotides and assembling the oligonucleotides into a gene in parallel, onto a single chip. A specific mismatch endonuclease is also used in the process to establish an error repair system in gene synthesis, and the error rate is decreased to about 0.19 mismatched bases/kb. The high-throughput, high-fidelity and low-cost chip process of gene synthesis provided in the present invention can meet the requirements of gene synthesis and the optimization and screening of protein expression on a large scale at the frontier of life sciences such as synthetic biology, genomics, and systems biology.

8 Claims, 3 Drawing Sheets

GENE SYNTHESIS PROCESS, GENE CHIP AND KIT

This application is a National Stage application of PCT international application PCT/CN2012/074181, filed on Apr. 17, 2012 which claims the priority of Chinese Patent Application No. 201210068841.7 entitled "GENE SYNTHESIS PROCESS, GENE CHIP AND KIT", filed with the Chinese Patent Office on Mar. 15, 2012, both of which are incorporated herein by reference in their entirety.

FIELD OF THE INVENTION

The present invention relates to the field of biotechnology, particularly to the field of gene chip, and specifically discloses a high-throughput, high-fidelity method of gene synthesis, as well as a gene chip and a kit.

BACKGROUND OF THE INVENTION

Low-cost, high-throughput gene synthesis and precise control of protein expression are the critical technical problems of synthetic biology. Currently, the main method for artificially synthesizing gene is to obtain long chain DNA by splicing and assembling short chain oligonucleotides. The cost of the method for artificially synthesizing short chain oligonucleotide by chemical method is very high (RMB 0.6 per nucleotide), and the error rate of synthesis remains as high as one base deletion per 100 bases and one mismatch or insertion per 400 bases. As a result, synthesis of gene or genome from assembling oligonucleotide is expensive, and the accumulative error rate of synthesis is high. Repairing errors by clone sequencing and mutagenesis methods further increases the amount of labor and total cost.

Oligonucleotide synthesis by performing large scale parallel synthesis on microfluidic chip can significantly reduce the cost. Currently, the method for synthesizing oligonucleotide on the chip mainly includes ink-jet printing (Agilent), 5'-end modified photolabile protecting groups (Nimblegen/Affymetrix), photo-generated acid deprotection (Atactic/Xeotron) and electrochemical method (Oxamer/Combimatrix). However, due to the very small surface area of the microfluidic chip, the yield of the oligonucleotide synthesis is low, with the concentration of each sequence of oligonucleotide in the solution being $10^{-12}$ M or less. Thus, extensive amplification is required prior to assembling into gene. Currently, a feasible method is as follows: releasing the synthesized oligonucleotide from the microfluidic chip by chemical or enzymatic treatment, amplifying by PCR, digesting by restriction enzyme, and purifying, then assembling the obtained oligonucleotide into gene or genome, and the error repair method of the gene synthesis mainly involves polyacrylamide gel electrophoresis and HPLC. Since the current methods of gene synthesis and error repair are still compromised by cumbersome steps, new strategies are urgently required to increase integration and miniaturization, lower cost, and increase the efficiency in synthesis and error repair.

SUMMARY OF THE INVENTION

The present invention intends to provide a high-throughput, high-fidelity, low cost gene synthesis method, which integrates the steps of oligonucleotide pool amplification and parallel gene assembly on one microfluidic chip to perform simultaneously, and also employs mismatch-specific endonucleases to establish an efficient error-repair system for gene synthesis, which decreases the error rate of synthesis from about 1.9 error base per kb to less than 0.19 error base per kb. The method presents a cost that is one-tenth of the lowest reported cost.

The invention provides a method of gene synthesis, wherein isothermal nicking and strand displacement amplification, and polymerase cycling assembly reactions are performed on one gene chip to achieve oligonucleotide amplification and gene assembly, the gene chip is formed by immobilizing oligonucleotides to the surface of a solid substrate. The oligonucleotide has at 3'-end a linker sequence of 15-150 bases and is anchored onto the surface of the chip via a nicking endonuclease recognition site within the linker sequence.

Preferably, the length of the synthesized gene is greater or equal to 200 base pairs.

Preferably, the method further comprises and employs mismatch-specific endonuclease to perform the gene synthesis error-repair step.

Preferably, the three reactions of oligonucleotide amplification, assembly and gene synthesis error-repair are carried out successively or stepwise in the same system.

Preferably, the gene synthesis error-repair reaction is carried out on-chip or separately off-chip.

Preferably, the gene chip can be divided into one or more sub-areas, and oligonucleotide amplification and gene assembly are simultaneously carried out in one or more sub-areas.

Preferably, a universal primer is used to hybridize to the linker at 3'-end of the oligonucleotides in the isothermal nicking and strand displacement amplification and polymerase cycling assembly reactions. While the strand displacement polymerase extends and displaces the oligonucleotide, the nickning endonuclease separates the universal primer from the newly amplified oligonucleotide chain to re-free 3'-end of the universal primer for new extension reaction.

Preferably, the gene synthesis error-repair step is carried out by heat denaturing and re-annealing the synthesized gene to expose the mismatch site; recognizing and cleaving the mis-match site by the mismatch-specific endonuclease and 3'→5' exonuclease activities; assembling the resulting gene fragments into a complete gene by overlap-extension PCR reaction.

Another purpose of the present invention is to provide a gene chip formed by immobilizing oligonucleotide probes onto the surface of a solid substrate, wherein the oligonucleotides has at 3'-end a linker sequence of 15-150 bases and is anchored onto the surface of the chip via a nicking endonuclease recognition site within the linker sequence.

Preferably, for the gene chip, the microarray is divided into sub-arrays by using the method of physical segmentation, and each sub-array contains oligonucleotide sequence for synthesizing more than 0.2 kb in total length.

The solid substrate used in the gene chip of the present invention is selected from any material that is suitable for the preparation of a gene chip, including but not limited to nitrocellulose membrane, nylon membrane, glass slide, silicon wafer and plastic sheet. The gene chip of the present invention is prepared by immobilizing oligonucleotides onto the substrate through successively dotting the oligonucleotides onto the substrate and anchoring the oligonucleotides by means of a nicking endonuclease recognition site within the 3'-end linker sequence.

The present invention further provides a gene synthesis kit comprising any gene chip as described above, a nicking endonuclease, a strand displacement DNA polymerase, a high-fidelity DNA polymerase and a mismatch-specific endonuclease.

Preferably, the kit of the present invention further comprises dNTP, BSA, a nicking endonuclease, a strand displacement polymerase, a high-fidelity DNA polymerase, Thermopol II buffer and oligonucleotide primers, wherein the Thermopol II buffer consists of 20 mM Tris-HCl, 10 mM $(NH_4)_2SO_4$, 10 mM KCl, 2 mM $MgSO_4$, and 0.1% Triton X-100, pH 8.8 at 25° C.

The method of the present invention is a microarray-based high-throughput gene synthesis technique. The microarray is divided into sub-arrays by using the method of physical segmentation, and each sub-array only contains synthetic oligonucleotide sequence of more than 0.2 kb in total length, thus can avoid selective amplification of sequence, and can effectively synthesize all the DNA sequences, and finally assemble the final DNA by using the total length DNAs synthesized in each sub-array, thereby avoiding the cross-hybridization of similar sequences to achieve an effective assembly of a gene.

Chemical methods are currently widely used to treat the oligonucleotide sequence, so as to cleave oligonucleotides from the chip for subsequent off-chip assembly reactions. The present invention, for the first time, employs nicking and strand displacement amplification reaction to amplify oligonucleotides from the surface of the microarray. That is to say, the 25-mer universal ligand for anchoring the sequence onto the surface of the chip contains a nicking endonuclease recognition site. After synthesis, the oligonucleotide sequences can be released by adding nicking endonuclease which catalyzes the release of the sequence, for performing sequence assembly.

In order to avoid the downstream complex operations of gene collection and purification required by the assembly reaction of the genes, polymerase cycling assembly reaction can take place immediately after nSDA reaction without a buffer change, which achieves the oligonucleotide synthesis and assembly into gene fragments take place in the same chamber. The error rate of gene synthesis achieves ~0.19 error/kb, by using a special mismatch-specific endonuclease CEL enzyme to reduce the error of gene synthesis.

The high-throughput, high-fidelity method for synthesizing gene based on microfluidic chip technique of the present invention can substantially reduce the cost of gene synthesis, significantly reduce the time for synthesis, and greatly meet the urgent demand for large-scale gene synthesis in the frontier field of life science.

Terms and Definitions

The term "nicking endonuclease" refers to a DNA endonuclease that cuts only one strand of the double-strand of DNA.

The term "strand displacement amplification" refers to a method for in vitro DNA amplification at a condition of constant temperature.

The term "universal primer" refers to primers that can bind certain type of vector DNA, and are suitable for all the cloned DNAs established by the vector.

The term "polymerase cycling assembly" refers to such a method that involves stepwise extending oligonucleotide fragments hybridized by overlapping at both ends through heat cycle reaction by directly using thermophilic DNA polymerase, and finally synthesizing the full length gene.

The term "mismatch-specific endonuclease" refers to an enzyme that can cleave all types of DNA double-strand mismatches caused by base mutation, insertion or deletion.

(a) shows 1,296 *E. coli* colonies expressing different lacZα codon mutant genes sorted by color intensity.

In (b), the bar graph shows the distribution of color intensities of 1,468 random colonies expressing different lacZα codon mutant genes on an agar plate.

Figure 4:
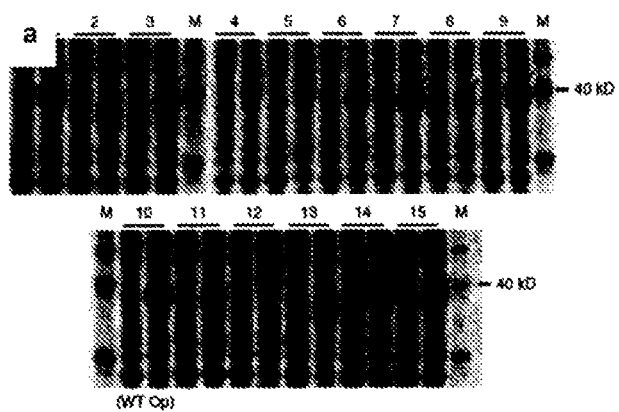
Figure 4:
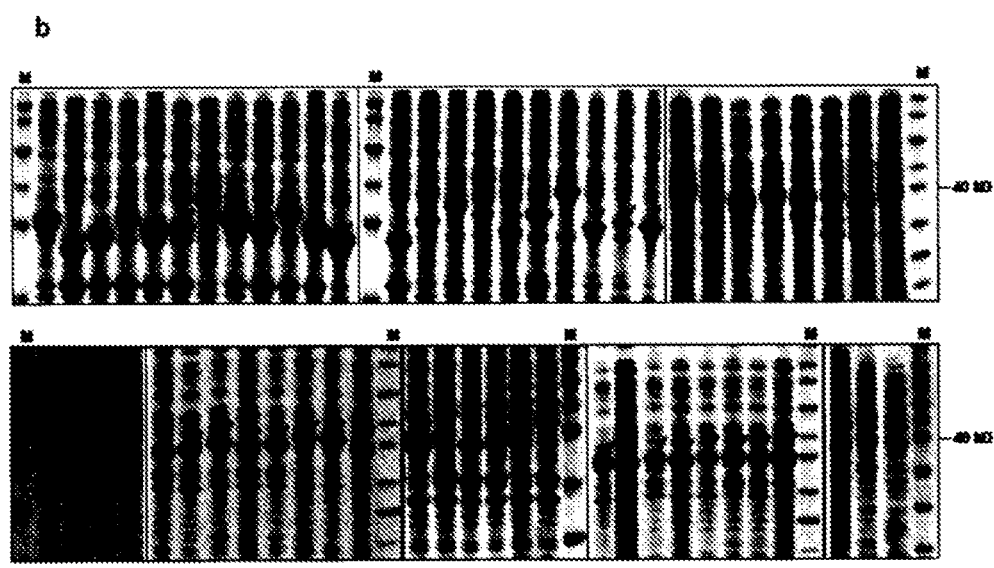

FIG. 4 shows the optimization result of protein expression by the using the high-throughput, high-fidelity chip gene synthesis technique of the present invention.

FIG. (*a*) lists the data of 15 proteins therein. Each pair of lanes represent the total protein within the *E. coli*, with the wild-type (WT) on the left lane, and the optimized clone (Op) on the right. The thicker band indicated by the arrow is highly expressed wild-type transcriptional factor-GFP fusion protein. Lane M represents molecular weight marker.

FIG. (*b*) shows the results of the remaining 59 proteins.

DETAILED EMBODIMENTS

The present invention discloses a high-throughput, high-fidelity gene synthesis method, a chip and the use thereof. Those skilled in the art can use the content herein for reference, and modify the process parameters to achieve the present invention. It should be noted that all the similar alterations and modifications are apparent to those skilled in the art, and are deemed to be within the present invention. The chip and its use of the present invention are illustrated by preferred examples, related personnel apparently can make certain alterations or appropriately modify and combine the method and used described herein to achieve and apply the technique of the present invention without departing from the content, spirit and scope of the present invention.

Figure 1:
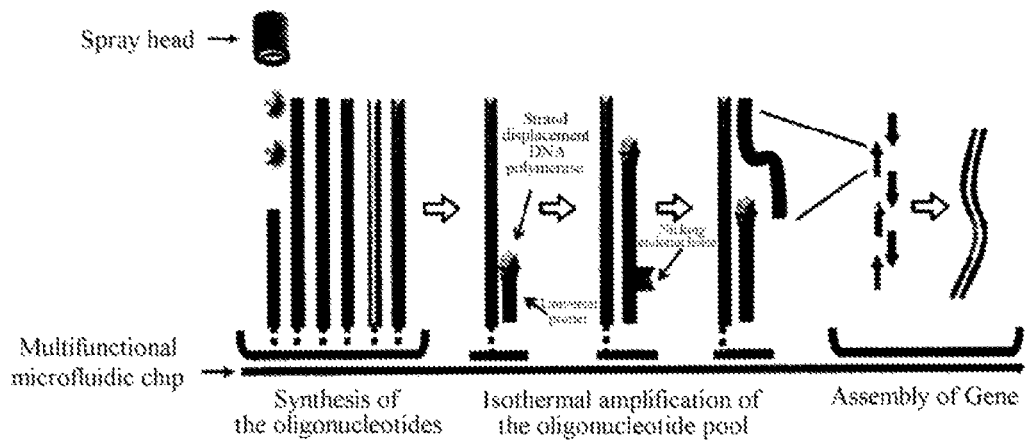
FIG. 1 is a schematic diagram showing the overall process of integrating the oligonucleotide amplification and gene assembly process on the same chip.

The overall process of gene synthesis method provided by the present invention is shown in FIG. 1, wherein the amplification of nucleotides and the gene assembly process are integrated on the same chip. Oligonucleotide pool is synthesized in each individual microcell of the microfluidic chip by ink jet DNA chip synthesizer or other type of chip synthesizer. Then the combined reaction mixture for amplification and assembly is added to the microcell and sealed. In a nicking and strand displacement amplification reaction (nSDA), the strand-displacing DNA polymerase extends and displaces the proceeding strand while the nicking endonuclease separates the universal primer from the synthesized oligonucleotide product, and generates new 3'-end for further extension. After amplification, free oligonucleotides in each microcell are assembled by polymer chain reaction (PCR) to form gene product.

In order for those skilled in the art to better understand the technical solution of the present invention, the present invention is further illustrated in details in conjunction with specific examples, which are intended to illustrate but not to limit the present invention.

Example 1: Design and Preparation of the Chip

Figure 3:
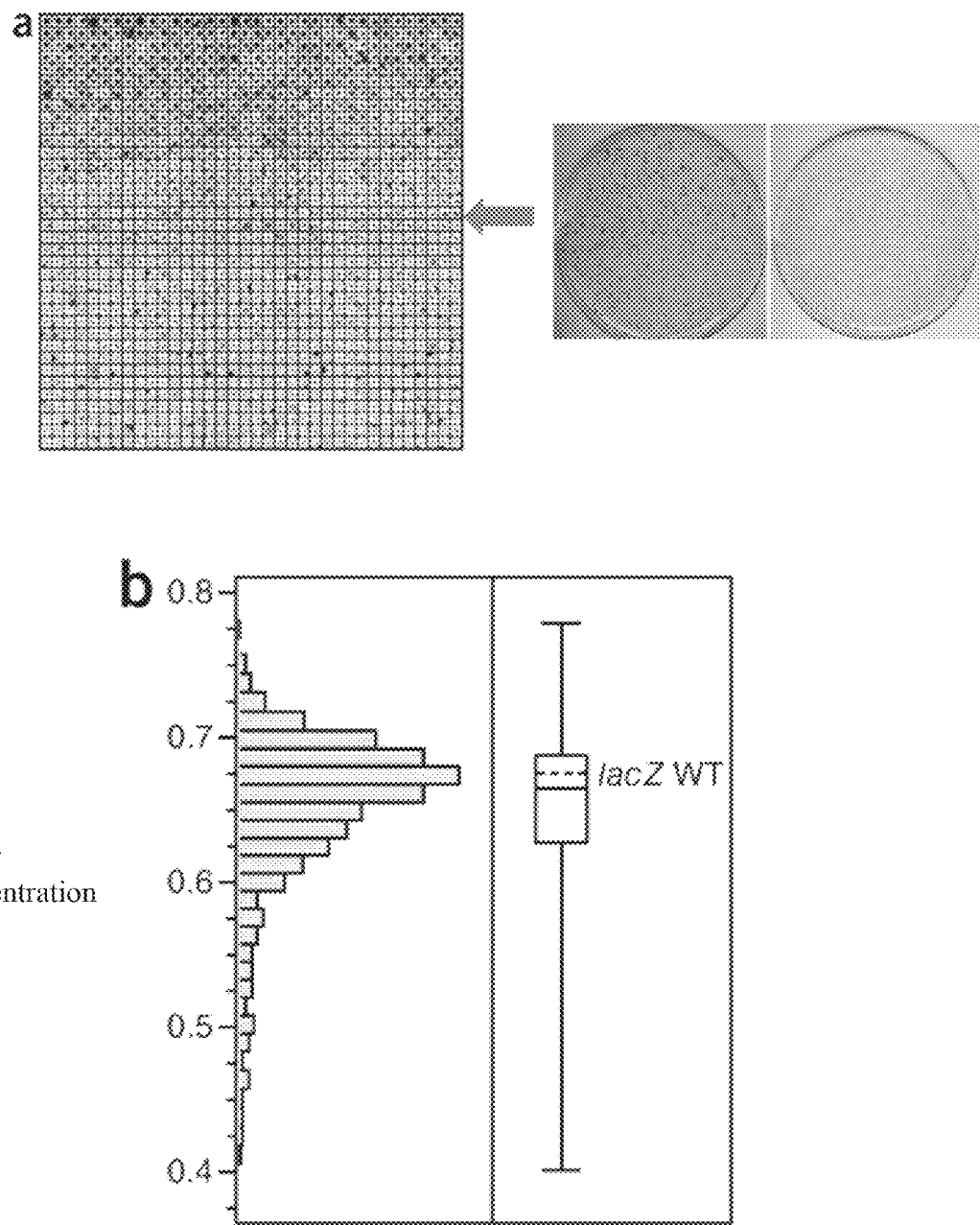
FIG. 3 shows the expression in *E. coli* of synthetic lacZα codon mutant genes synthesized on a chip by applying the method of the present patent.

The surface of a standard 1"×3" cyclic olefin copolymer (COC) flake is modified by silicon film, and the surface of the entire chip is divided into 30 microcells. The radius of each microcell is 150 μm and the distance between the center points is 300 μm, so as to reduce edge-effects which lead to undesired oligonucleotide synthesis. FIG. 3 is the schematic diagram of the array of microcells on the surface of the microfluidic chip modified silica film.

Example 2: On-Chip Synthesis of Oligonucleotides

The ink jet printing method for synthesizing oligonucleotide is known. Oligonucleotides were synthesized on cyclic olefin copolymer (COC) chips modified by silicon film, using a custom-made ink jet DNA chip synthesizer. The length of the oligonucleotide product is designed to be 48 or 60 bases with a 25-mer linker sequence at the 3'-end. This linker contained a recognition site of nicking endonuclease and anchored the oligonucleotide to the chip surface. 361 spots could be printed in each microcell in the chip and on each point was synthesized a nucleotide of one sequence. The oligonucleotide synthesized in each microcell will respectively be assembled into one gene of more than 0.2 kb in length or one gene library. Multiple spots were used to synthesize the oligonucleotide of one sequence to improve the yield.

Example 3: On-Chip Amplification of Oligonucleotide and Gene Assembly

After oligonucleotide synthesis, each microcell on the chip was added with a mixture of other components required by the combined reaction of isothermal nicking and strand displacement amplification (nSDA) and polymerase chain assembly (PCA), containing 0.4 mM dNTP, 0.2 mg/ml BSA, nicking endonuclease (Nt.BstNBI, purchased from NEB, US), strand-displacing DNA polymerase (Bst DNA polymerase large fragment, purchased from NEB, US) and high-fidelity DNA polymerase (Phusion polymerase, purchased from NEB, US) and optimized Thermopol II buffer (purchased from NEB, US). After each microcell on the chip was sealed, the chip was placed on the chip adaptor of a Mastercycler Gradient PCR instrument (purchased from Eppendorf) to carry out combined nSDA-PCA reactions. First, nSDA reaction was performed, which involved incubation at 50° C. for 2 hr followed by 80° C. for 20 min; the subsequent PCA reaction involved an initial denaturation at 98° C. for 30 s, followed by 40 cycles of PCR reaction, each cycle included: denaturation at 98° C. for 7 s, annealing at 60° C. for 60 s and extending at 72° C. for 15 s/kb, and finished with an extended extension step at 72° C. for 5 min.

In a nicking and strand displacement amplification reaction (nSDA), a universal primer hybridized to the 3'-end linker of the oligonucleotides, and the DNA strand-displacing polymerase extends and displaces the proceeding strand, while the nicking endonuclease separates the universal primer from the oligonucleotide used for the gene synthesis assembly, and generates new 3'-end for further extension reaction.

After the nSDA-PCA reaction, 1-2 μl of the reaction product from each microcell was used for PCR amplification with Phusion polymerase and terminal primer. The concentration of the terminal primer was 0.5 μM. The PCR reaction involved an initial denaturation at 98° C. for 30 s, followed by 30 cycles of PCR reaction, each cycle included: denaturation at 98° C. for 10 s, annealing at 60° C. for 60 s and extension at 72° C. for 30 s/kb, and finished with a final extension at 72° C. for 5 min.

After amplification, the free oligonucleotides in each microcell were all assembled into gene products by polymer chain assembly (PCA) reaction.

Example 4: Synthesis Error Repair System

Figure 2:
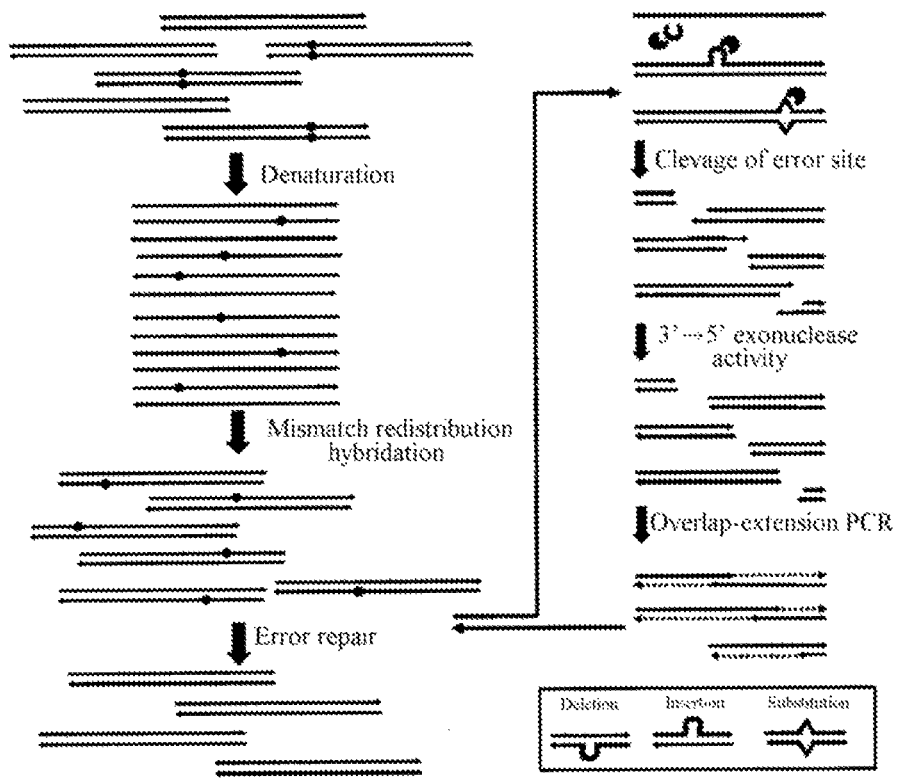
FIG. 2 is a schematic diagram showing the reaction principle of the error repair system of gene synthesis.

Mismatch-specific endonucleases of plant CEL family were used in the present invention, which can recognize and cleave all types of mismatches caused by base substitutions or small insertions or deletions. A commercial subtype of the CEL enzyme was the Surveyor nuclease (purchased from Transgenomic). In an error repair reaction, the synthetic genes were firstly heat-denatured and re-annealed to expose the mismatch sites, and then treated these genes with Surveyor nuclease, the mismatch sites were recognized and cleaved by mismatch-specific endonuclease and 3'→5' exonuclease activities. Finally, the resulting gene fragments were re-assembled into complete gene by overlap-extension PCR. This repair process can be repeated to increase the repair rate. After two rounds of repair, the errors in the synthesized genes can be reduced by 16-fold or more, yielding a final error rate of 1 error base in 8700 bp. The reaction mechanism of gene synthesis error repair is shown in FIG. 2.

After PCR amplification and purification, the chip-assembled gene products were diluted with 1×Taq buffer (purchased from NEB) or 1×Phusion HF buffer (purchased from NEB) to a final concentration of 50 ng/μl, and were pre-denatured at 95° C. for 10 min, and annealed by gradually cooling down, which involved firstly cooling down to 85° C. at a rate of 2° C./s, then cooling down to 25° C. at a rate of 0.3° C./s, holding for 1 min at every 10° C. interval. The reaction product (4 μl, 200 ng) was mixed with 0.5 μl of Surveyor nuclease reagents and 0.5 μl enhancer (purchased Transgenomic) and incubated at 42° C. for 20 min. The reaction product was treated by overlap-extension PCR to re-assemble the gene fragments cleaved due to containing error base into complete gene. The PCR reaction involved an initial denaturation at 98° C. for 30 s, followed by 30 cycles of PCR reaction, each cycle included: denaturation at 98° C. for 10 s, annealing at 60° C. for 60 s and extension at 72° C. at a rate of 30 s/kb, and finished with a final extension at 72° C. for 5 min.

In the second round of error repair, the product from the previous round was diluted to 50 ng/μl using 1×Taq buffer and re-annealed, with the reaction system and conditions described above. The reaction product was treated by overlap-extension PCR, and the resulting products were the repaired complete genes.

Example 5: Expression Screen of lacZα Codon Mutant Gene

Expression of lacZα makes the host *E. coli* colonies turn blue in the presence of isopropyl-β-D-thiogalactoside (IPTG). Firstly, a series of lacZα codon mutant genes were designed by referring to the unbiased codon usage table, in which table, the codons representing the same amino acid were used in the same frequency.

Then, a lacZα codon mutant gene pool consisting of 1,296 different lacZα codon mutant genes were constructed, and all of them were transformed into *E. coli* competent cells. A small fraction was coated on solid agar plate and the blue color intensity of the each monoclonal colony was measured in real time by automated image analysis. The difference in the color intensity of the colonies represented the difference in protein expression level. Randomly picked monoclonal colonies on the solid agar plate and performed statistical analysis, to obtain the bell-shaped distribution of the expression level of codon mutant genes. Approximately one-third of the mutant gene showed higher expression levels than wild-type lacZα. The expression level of the wild-type gene was slightly higher than the median level of all the clones with measurable expressions.

FIG. 3 shows the expression in *E. coli* of lacZα codon mutant gene synthesized on the chip by the method of the present invention. FIG. 3a shows 1,296 *E. coli* colonies expressing different lacZα codon mutant genes sorted by color intensity. Raw images were acquired by scanning an agar plate on a HP Photosmart C7180 Flatbed Scanner. The bar graph in FIG. 3b shows the distribution of color intensities of 1,468 random colonies expressing different lacZα codon mutant genes on an agar plate. Owing to the large size of the codon mutant gene pool synthesized on the chip, the probability of having identical clones on one plate was extremely low, as confirmed by sequencing several hundreds of blue colonies. The expression level of the wild-type lacZα is presented with a dash line.

Although the cause of this distribution requires further study, the distribution allowed us to estimate the potential translational ability of the lacZα gene in *E. coli*. These experimental results showed that the on-chip gene synthesis method disclosed by the present patent disclosure achieved screening a gene sequence with reliable and desired protein expression level in a given expression system, with high feasibility and reliability.

Example 6: Expression Screen of *Drosophila* Transcription Factor Protein Domains To allow direct measurement of protein expression levels in *E. coli*, each target gene was tagged with green fluorescent protein (GFP) reporter gene tag. Proteins expressed at higher levels will result in colonies with brighter fluorescence.

The present invention were applied to optimize the expression of 74 *Drosophila* transcription factor protein domains, these proteins were used for preparing antibodies of the ENCODE project (Encyclopedia of DNA Elements). Firstly, 15 candidate genes which were not expressed in *E. coli* were tested. According to the *E. coli* codon-usage table, codon mutant gene pool were designed and synthesized by using the on-chip gene synthesis method of the present patent disclosure. The mismatch endonuclease error repair system was not used in this application, because heteroduplexes DNA might be formed between very closely related codon mutant genes. The synthesized genes were fused to the N-terminus of GFP and inserted into the pAcGFP expression vector using the sequence-independent circular polymerase extension cloning method (CPEC). *E. coli* cells were transformed by the plasmid and cultured on agar plates. GFP fluorescence from all colonies was monitored continuously and some highly fluorescent clones were picked for sequencing. The plasmids contained in all clones carrying different codon mutant genes were throughout the sequence of the candidate proteins.

The sequence-confirmed, highly fluorescent clones were cultured in liquid media and the expression of the protein domains was determined by performing electrophoresis of the total protein extracts on polyacrylamide gels. High-expression clones were identified for all 15 candidates using this strategy. In comparison, the wild-type controls cloned into the same vector and cultured under the same conditions showed undetectable protein expression. This result indicates that the on-chip gene synthesis method of the present patent disclosure is capable of reliably increasing protein expression from an undetectable level to as high as representing 50-60% of the total cell protein mass.

FIG. 4 shows the results of the optimization of protein expression by using the high-throughput, high-fidelity on-chip gene synthesis technique. Data for 15 proteins are listed in FIG. 4a. Each pair of lanes shows total cell protein extract of *E. coli* expressing the wild-type (left lane, WT) and optimized (right lane, Op) clones. The broad bands indicated by the arrow represent highly expressed wild-type transcription factor-GFP fusion proteins. There was no detectable expression of wild-type transcription factor-GFP fusion proteins in the wild-type lanes. Equal amounts of the total cell protein extracts were separated on NuPage 4-12% gradient gels and stained with EZBlue gel staining reagent. Lane M is Novex pre-stained protein molecular weight marker (purchased from Invitrogen).

FIG. 4b shows the protein expression results for the remaining 59 proteins, which were optimized by the same codon optimization method.

In this Example, 74 *Drosophila* transcription factor gene fragments were optimized and then expressed in *E. coli* by synthesizing about 1,000-1,500 codon mutant gene against each gene fragment, cloning them in-frame with GFP gene, and screening for the colonies with the highest fluorescence. Sequencing and protein gel electrophoresis results confirmed that all candidate proteins tested obtained high-expression clones as predicted. Accordingly, the feasibility and reliability of the present invention were further confirmed.

Those described above are only specific Examples of the present invention. However, the protection scope of the present invention is not limited hereto. Modifications and substitutions easily conceived by those skilled in the art within the technical scope disclosed by the present invention should all be contained within the protection scope of the present invention.

A high-throughput, high-fidelity gene synthesis method, as well as a chip and the use thereof proposed by the present invention are illustrated by means of Examples. Those of skill in the art apparently can make alterations or appropriately modify and combine the high-throughput, high-fidelity gene synthesis method, the chip and the use thereof described herein to achieve the technique of the present invention without departing from the content, spirit and scope of the present invention. It should be specifically noted that all similar substitutions and alterations are apparent to those skilled in the art, and they are all deemed to be within the spirit, scope and content of the present invention.

The invention claimed is:
1. A method of gene synthesis, comprising the steps of:
 (1) immobilizing a pool of oligonucleotides to the surface of a solid substrate to form a gene chip, wherein the oligonucleotides are anchored to the surface of the chip via a linker sequence that is 15-150 bases in length, located at the 3' end, and contains a nicking endonuclease recognition site;
 (2) carrying out oligonucleotide pool amplification on the gene chip by performing an isothermal nicking and strand displacement amplification reaction, which comprises performing the following steps under isothermal conditions: (i) hybridizing a universal primer to the linker at the 3' end of the chip-immobilized oligonucleotides, (ii) extending the universal primer using a strand displacement polymerase to form a newly amplified oligonucleotide chain, (iii) nicking the newly amplified oligonucleotide chain using a nicking endonuclease to re-free the 3' end of the universal primer for a new extension reaction, and (iv) using the strand displacement polymerase to extend the universal primer of step (iii) and displace the newly amplified strand generated in step (ii), and (3) carrying out parallel gene assembly on the gene chip by performing a polymerase cycling assembly reaction using the newly amplified oligonucleotide chains generated in the oligonucleotide pool amplification step.

2. The method of gene synthesis according to claim 1, wherein the length of the synthesized gene is greater than or equal to 200 base pairs.

3. The method of gene synthesis according to claim 1, wherein the method further comprises a step of (4) carrying out gene synthesis error repair using a mismatch-specific endonuclease.

4. The method of gene synthesis according to claim 3, wherein the oligonucleotide pool amplification, the parallel gene assembly, and the gene synthesis error repair are carried out successively or stepwise in the same system.

5. The method of gene synthesis according to claim 3, wherein the gene synthesis error repair is carried out on-chip.

6. The method of gene synthesis according to claim 3, wherein the gene synthesis error repair is carried out by heat denaturation and re-annealing the synthesized gene to expose a mismatch site(s); recognizing and cleaving the mismatch site(s) using the mismatch-specific endonuclease and a 3'→5' exonuclease; and assembling the resulting gene fragments into a complete gene by overlap-extension PCR.

7. The method of gene synthesis according to claim 3, wherein the gene synthesis error repair is carried out separately off-chip.

8. The method of gene synthesis according to claim 1, wherein the gene chip is divided into one or more sub-areas, and the oligonucleotide pool amplification and the parallel gene assembly are simultaneously carried out in the one or more sub-areas.

\* \* \* \* \*